United States Patent [19]

Harnly et al.

[11] 4,300,833
[45] Nov. 17, 1981

[54] METHOD FOR BACKGROUND CORRECTED SIMULTANEOUS MULTIELEMENT ATOMIC ABSORPTION ANALYSIS

[75] Inventors: James M. Harnly, Rockville; Thomas C. O'Haver, Silver Spring; Wayne R. Wolf, Brookeville, all of Md.; Bruce M. Golden, Warminster, Pa.

[73] Assignee: The United States of America as represented by the Secretary of Agriculture, Washington, D.C.

[21] Appl. No.: 88,665

[22] Filed: Oct. 26, 1979

[51] Int. Cl.³ .......................... G01J 3/36; G01N 21/74
[52] U.S. Cl. .................................... 356/307; 356/312; 364/498
[58] Field of Search ............... 356/307, 311, 312, 315; 364/498

[56] References Cited

U.S. PATENT DOCUMENTS

| | | |
|---|---|---|
| 3,472,594 | 10/1969 | Hughes et al. |
| 3,532,429 | 10/1970 | Hughes et al. |
| 3,588,252 | 6/1971 | Habosian .......................... 356/307 |
| 3,752,585 | 8/1973 | Elliott |
| 3,822,098 | 7/1974 | Rudder et al. |
| 3,901,599 | 8/1975 | Meric |
| 3,985,441 | 10/1976 | Schoeffel et al. |
| 4,030,828 | 6/1977 | Sonobe et al. |
| 4,049,353 | 9/1977 | Missio |

OTHER PUBLICATIONS

*Analytical Chemistry*, vol. 51, No. 12, Oct. 1979, pp. 2007–2014.

Zander., et al, *Analytical Chemistry*, vol. 48, No. 8, Jul. 1976, pp. 1166–1175.
Epstein et al., *Applied Spectroscopy*, vol. 30, No. 3, May–Jun. 1976, pp. 324–329.
Skogerboe et al., *Applied Spectroscopy*, vol. 30, No. 5, Sep.–Oct. 1976, pp. 495–500.
Abstract No. 31, ACS/CSJ Chemical Congress; Honolulu, Hawaii, Apr. 1–6, 1969.
Abstract No. 216, ACS/CSJ Chemical Congress; Honolulu, Hawaii, Apr. 1–6, 1979.
Abstract No. 238, 1979 Federation of Anal. Chemistry and Spectroscopy Societies, Phila. Pa., Sep. 16–21, 1979.
Abstract No. 325, 1979 Pittsburgh Conference on Analytical Chemistry and Applied Spectroscopy, Cleveland, Ohio, Mar. 5–9, 1979.
Abstract 102, Fifth Annual Meeting, Federation of Analytical Chemistry and Spectroscopy Societies, Boston, Mass., Oct. 30–Nov. 3, 1978.

*Primary Examiner*—F. L. Evans
*Attorney, Agent, or Firm*—M. Howard Silverstein; William E. Scott; David G. McConnell

[57] ABSTRACT

A method and apparatus for simultaneous multielement atomic absorption analysis, comprising use of a continuum source and a high resolution echelle polychromator modified for wavelength modulation, and a high speed data acquisition system (SIMAAC). The method and apparatus is capable of measuring as many as 16 or more elements simultaneously with either flame, electrothermal or other means of atomization. Double beam operation and dynamic background correction are achieved on all channels. Linear dynamic range of up to six orders of magnitude can be achieved for each channel.

8 Claims, 7 Drawing Figures

METHOD FOR BACKGROUND CORRECTED SIMULTANEOUS MULTIELEMENT ATOMIC ABSORPTION ANALYSIS

BACKGROUND OF THE INVENTION

1. Field of the Invention

This invention relates generally to the field of atomic absorption spectrometric analysis, and in particular, to the field of simultaneous multielement atomic absorption spectrometric analysis.

2. Description of Prior Art

In recent years there has been considerable interest in the development of multielement atomic spectrometry systems. Most of these have been based on atomic emission or atomic fluorescence measurement; and in fact it has been said that, compared to these methods, atomic absorption is the least likely candidate for simultaneous multielement development. Nevertheless, atomic absorption has enjoyed wide acceptance and utilization as a trace element analysis tool both by spectroscopists and by scientists whose main interests are in areas other than spectroscopy itself. As a result, the operating principles, atomization devices, sample preparation and introduction procedures, and potential interferences are already familiar to many users. From this point of view it would seem that a multielement atomic absorption spectrometer has some merit after all.

There have been numerous attempts to develop a practical simultaneous multielement atomic absorption spectrometer. Most of these systems suffer from one or more serious limitations, such as the inability to utilize furnace atomizers, limitations in the number of channels, lack of background correction or double beam operation, or complex constructional requirements. Only three systems have been shown to be able to utilize electrothermal atomization devices. One such system (Lundberg and Johansson) used a carbon rod atomizer and a modified monochromator with three exit slits. Only three elements could be determined simultaneously. Background correction was accomplished by using a continuum source in addition to the multielement hollow cathode lamp. A minicomputer was used for data acquisition and processing. Detection limits were a factor of 2 to 4 higher than those obtained when the same atomizer was used with a commercially available atomic absorption spectrometer (AAS) operating in the single element mode. The deterioration of the detection limits was attributed to the time sharing of the data acquisition system, the higher noise and lower intensity of the multielement hollow cathode lamp, and "constructional compromises".

Another such system (Salin and Ingle) developed was similar, having a modified, multiexit slit monochromator. The instrument was restricted to the simultaneous analysis of four elements due to hollow cathode lamp intensity limitations. Reported detection limits were approximately an order of magnitude worse than those reported for commercially available atomic absorption (AA) instruments using electrothermal atomization in the single element mode of operation.

The third system (Alder, et al.) employed a direct reader with the furnace to analyze up to 9 elements simultaneously in the absorption mode. An array of hollow cathode lamps was used as the light source. The direct reader electronics were replaced by a custom-designed analog circuit which generated peak area information. However, there were no provisions for compensating for non-specific background absorption and source fluctuation noise. Detection limits were comparable to commercially available AA instruments using electrothermal atomization.

This invention includes the design, construction, and operation of a simultaneous multielement atomic absorption spectrometer which is based upon a high-intensity continuum primary source, a high-resolution, wavelength modulated direct reading echelle polychromator, and a high-speed computer data acquisition system. This instrument has been dubbed SIMAAC. A single element spectrometer based on the similar optical principles, called CEWM-AA, is known. SIMAAC overcomes many of the limitations of previous designs. As many as 16 or more elements may be measured simultaneously with either flame, furnace or other atomization source. Each channel operates in true double-beam, background corrected mode.

A significant factor in the success of SIMAAC is the use of both a continuum source and wavelength modulation with high speed data acquisition. Prior art multielement AA apparatus have, at times, used a continuum source for sequential multielement analysis. All such apparatus have uniformly yielded unacceptably poor results. Wavelength modulation has been used in single element techniques. Accordingly, those skilled in the art have had no reason to even suspect that the use of a continuum source and wavelength modulation in multielement AA analysis could yield results comparable to single-element analysis. On the contrary, those skilled in the art have believed that utilization of a continuum source and wavelength modulation in multielement AA analysis would inevitably produce poorer results than when either was used individually. With SIMAAC, however, it is possible for the first time to obtain simultaneous multielement data without significant signal-to-noise loss compared to single-element operation.

SUMMARY OF THE INVENTION

It is an object of this invention to provide a method and apparatus for multielement atomic absorption (AA) analysis.

It is another object of this invention to provide a method and apparatus for simultaneous multielement AA analysis.

It is yet another object of this invention to provide a method and apparatus for simultaneous multielement AA analysis utilizing double beam operation and dynamic background correction.

It is still another object of this invention to provide a method and apparatus for simultaneous multielement AA analysis utilizing either flame, furnace or other atomization source.

It is a further object of this invention to provide a method and apparatus for simultaneous multielement AA analysis utilizing a continuum primary source and a wavelength modulated direct reading high resolution polychromator.

It is a still further object of this invention to provide an apparatus for simultaneous multielement AA analysis for as many as 16 or more elements without significant signal-to-noise loss as compared to single-element analysis.

These and other objects of this invention, which will be apparent from the description herein, are accomplished by an apparatus comprising a high-intensity continuum primary source, a high-resolution, wavelength modulated direct reading echelle polychromator, means for atomizing samples to be analysed, and a high-speed computer data acquisition system. Wavelength modulation is achieved by a quartz refractor plate mounted on an optical scanner torque motor and positioned just behind the entrance slit of the polychromator. As many as 16 or more elements can be measured simultaneously in true double-beam, background corrected mode, without significant signal-to-noise loss as compared to single-element operation.

DETAILED DESCRIPTION OF THE PREFERRED EMBODIMENT

Conceptually, the background corrected simultaneous atomic absorption spectrometer (SIMAAC) consists of a continuum source, a high resolution direct reading polychromator modified for wavelength modulation, and a high speed data acquisition, storage, and processing system.

More specifically, the continuum source should provide intense continuum radiation over the entire 195 nm to 600 nm spectral range. The polychromator should have resolution comparable to the half width of atomic absorption profiles. The wavelength modulation is centered at the center of the absorption profile and extends to both sides of the profile. The wavelength modulation frequency must be sufficiently high to avoid the 1/f source flicker noise of the continuum source. In addition, the period of modulation should be smaller than the duration of the shortest absorption transient anticipated.

The data acquisition system sampling rate must exceed the wavelength modulation frequency by a factor equal to 10 times the maximum number of elements to be analyzed. A minimum of 10 discrete samplings per element per cycle are necessary to provide 5 to 6 orders of magnitude of linear dynamic range for calibration curves.

The data acquisition system must be capable of processing or storing the data acquired at the frequency above for a period of 30 seconds without missing a sample point. Storage of the data with processing afterwards is permissible.

Processing of the data is defined as ratioing the data taken at the two extremes of the wavelength modulation cycle with that acquired at the middle points. The log of this ratio is equivalent to absorbance. This definition of "data processing" provides background correction and a minimization of the continuum source flicker noise. Ratioing of points acquired at specific intervals during the wavelength modulation cycle also provides for the extended range (5-6 orders of magnitude of concentration) of the calibration curve. This "data processing" provides one or more absorbance versus time arrays.

Manipulation of the absorbance arrays varies according to the atomizer used and the specific demands of each analysis. The data processor must be sufficiently flexible to allow altering of the manipulation of the absorbance arrays.

Figure 1:
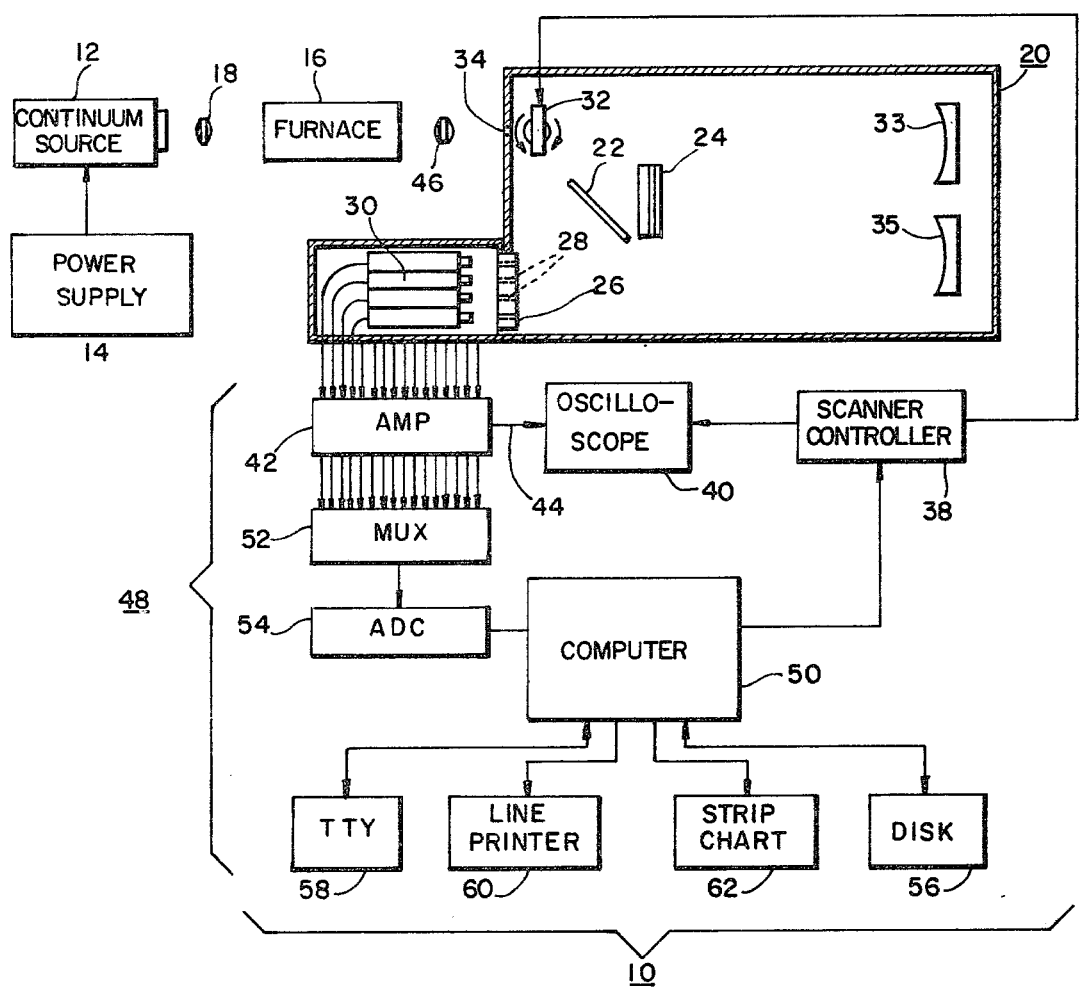
FIG. 1 is a block diagram of a simultaneous multielement atomic absorption spectrometer according to this invention.

A block diagram of a satisfactory construction 10 for (SIMAAC) according to this invention, is shown in FIG. 1. A suitable primary light source is the Eimac 300 watt xenon arc lamp 12 (VIX-UV) and Power Supply 14 (PS 300-11) manufactured by Varian Eimac Division. Previous measurements have shown that the intensity of this lamp over a typical atomic absorption profile is actually greater than that of conventional hollow cathode lamps, even for the As and Se wavelengths below 200 nm.

The atomizer 16 can be a conventional flame, a graphite furnace, or other device. A suitable atomizer is an unmodified Perkin-Elmer HGA-2100 graphite furnace, which also has its own power supply, not shown. A focusing lens 18 is disposed between the continuum source 12 and the furnace 16.

A suitable spectrometer 20 is a Spectraspan 111 Echelle polychromator, manufactured by Spectrametrics, Inc. This is a very compact 20-channel direct reader utilizing an echelle grating 22 in conjunction with an order-separating prism 24. The echelle spectrometer focuses the dispersed spectrum as a two dimensional array onto a removable mask or "cassette" 26 in which the exit apertures or slits 28 are located, as distinguished from, the single element mode, wherein a single slit with conventional height and width controls is mounted in the cassette. Operation of the polychromator is fully described in U.S. Pat. No. 4,049,353, the teachings of which are incorporated herein. Briefly, for the multielement mode, up to 20 slits of a pre-specified height and width are appropriately positioned on the cassette face. Pinhead mirrors within the cassette direct the light from the slits to a fixed array of up to 20 end-on photomultiplier tubes. In the present embodiment, the array of photomultiplier tubes 30 comprises 20 such tubes, any 16 of which can be monitored simultaneously by the 16 channel computer described herein. Once selected, the 20 slits cannot be relocated easily. However, the cassettes are easily changed, requiring only a few seconds to remove one and insert another.

Figure 2:
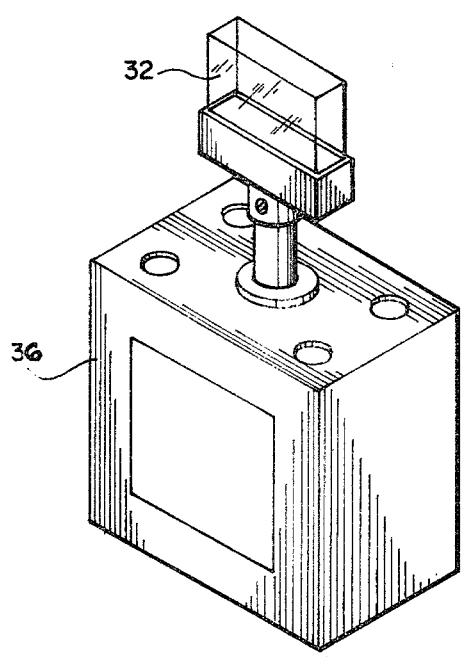
FIG. 2 is a perspective view of the wavelength modulator shown in FIG. 1.

The polychromator is modified by installing a quartz refractor plate wavelength modulator 32, shown in more detail in FIG. 2. The refractor plate 32 is positioned just behind the entrance aperture or slit 34 so that the entire spectrum at the focal plane can be modulated. The plate is mounted on an optical scanner torque motor 36. A suitable motor 36 and scanner controller 38 are the G-300 PD Motor and ccx-101 controller, manufactured by General Scanning, Inc. The motor has a position-sensing winding which provides an output voltage proportional to the actual refractor plate rotation angle (and thus to the wavelength displacement). It is possible, and often very useful, to observe the actual absorption profile of one of the channels in real time by driving the x-axis of an x-y oscilloscope 40 from this position output and the y axis from the photomultiplier tube preamp 42 output 44. A further focusing lens 46 is disposed between the furnace 16 and the entrance slit 34.

Within the monochromator 20, light passes through the quartz refractor plate 32, and is reflected by collimating mirror 33 through prism 24. The light is then reflected by the echelle grating 22, back through another portion of prism 24 and onto focusing mirror 35. Focusing mirror 35 directs the light to the various exit slits 28 of cassette 26.

The photoanodic current from each of the 20 photomultiplier tubes 30 is amplified by an array 42 of simple preamplifier circuits each consisting of a current-to-voltage converter and a non-inverting amplifier as known to those skilled in the art. The gain of each preamp and the high voltage supply of each phototube is individually adjusted so that the preamp outputs are all close to 10 volts when no absorption occurs. This insures that the full range of the analog-to-digital converter (ADC) is utilized for each channel.

Data is acquired from any 16 of the preamp outputs (at the rate of approximately 1000 readings per second per channel) by means of a minicomputer-based data system 48 comprising a PDP 11/34 minicomputer 50 equipped with a 16 channel multiplexer 52, a 12 bit (0–10,24 V.) analog-to-digital converter (ADC) (AD11-K) 54, a 4 channel, 12 bit (−10 V. to +10 V.) digital to analog converter (AA11-K), a dual programmable real time clock (KW11-K), a general purpose, digital, 16 bit input/output interface (DR11-K), and a disk drive controller (RK11-D). Mass storage preferably consists of two RK05 disks 56 (1.25 million words each); one fixed and one removable cartridge. Communication with the system is accomplished with a VT55 decscope (terminal and graphic display) 58 and an LA180 line printer 60. The serial number designations are those of Digital Equipment Corporation. It will be appreciated that many such systems and components are known to these skilled in the art, and are suitable for SIMAAC analysis. Such systems do not form a part of this invention, in and of themselves. The RT-11 (version 3) operating system is presently preferred.

Figure 3A:
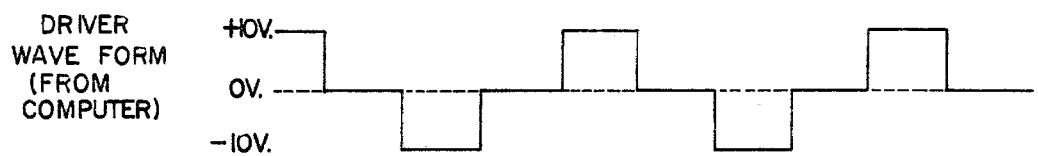
FIGS. 3($a$-$c$) is a timing scheme for wavelength modulation, data acquisition, and data reduction.
Figure 3B:
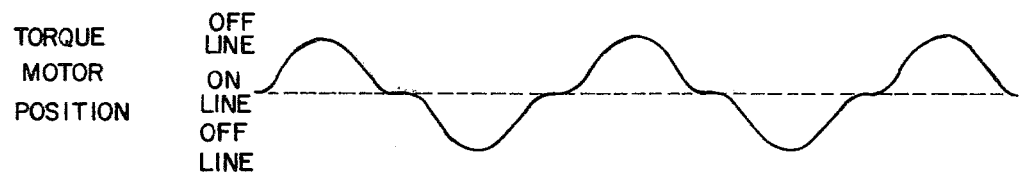
Figure 3C:
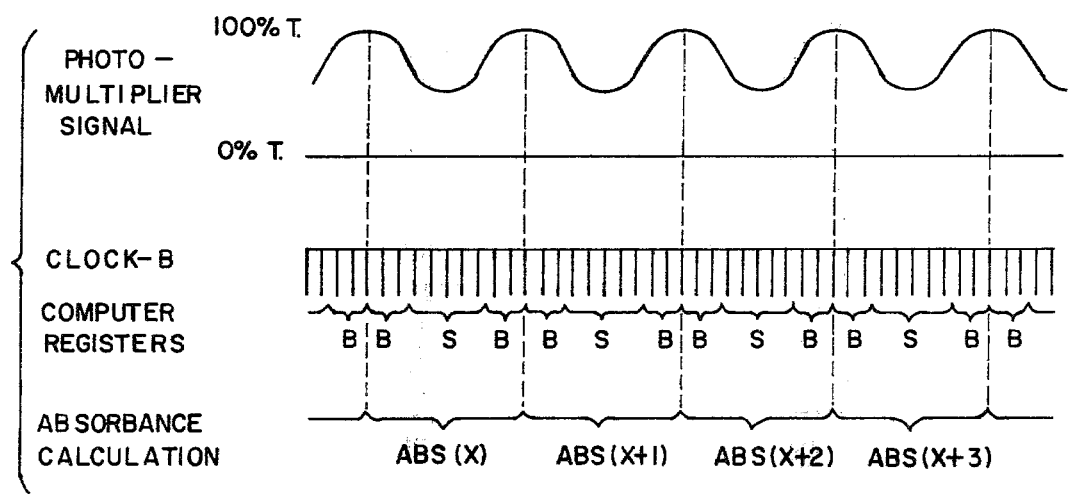

The time relationship between the wavelength modulation and the sampling of intensity data from any one of the 16 channels is shown in FIG. 3. The computer drives the scanner motor controller through one of its digital-to-analog converters (DAC). The modulation waveform is the 3-stepped waveform in FIG. 3(a). The middle step is centered on the atomic line of interest so that intensity readings can be made on the line and off the line on both sides. The corresponding torque motor position is shown in FIG. 3(b). During each half-cycle of the modulation waveform the computer takes five readings of the signal voltage on the line and five readings off the line for each of the 16 channels. Each set of ten readings for any one channel defines one point on the absorbance-time curve of that channel.

An assembly language program is used for data acquisition to meet the following modulation frequency and sampling rate requirements:

1. The frequency of wavelength modulation must be sufficiently high to avoid the 1/f source flicker noise of the Eimac lamp which has been observed below 50 Hz. The wavelength was modulated at 56 Hz, using the "stepped" waveform shown in FIG. 3(a). With this waveform, the intensity modulation produced by an atomic line in the center of modulation interval occurs at twice the frequency of wavelength modulation, i.e., at 112 Hz in this case, well above the 1/f noise region.

2. The period of modulation should be much smaller than the duration of the shortest absorption transient anticipated. With the HGA-2100 atomizer operated near its maximum temperature, volatile elements such as Zn and Pb produce absorption pulses which may have a duration as short as 0.2 to 0.5 sec. Thus, the 112 Hz modulation frequency provides adequate time resolution.

3. The sampling rate should be 160 (10 multiplied by 16 elements) times greater than the modulation frequency. The maximum sampling rate is limited by the ADC conversion time and the software overhead required to increment the multiplexer channel, to move the data from the ADC buffer to the data buffer, and to count conversions. For this work an overall sampling rate of 20.8 kHz was used. The sampling was multiplexed so that the 16 channels were read sequentially, which resulted in a channel sampling rate of 1.12 kHz per channel for each of the channels. This allowed five readings each of $I_o$ and I on each channel during each half-period of the wavelength modulation waveform.

4. Because of the high data rate, it was impossible to compute absorbance in real time from the intensity data using this data processor. Therefore, the raw data is stored without processing during the atomization and is processed during the interval between atomizations when the furnace is cooling down and drying and ashing the next sample.

5. A typical furnace atomization duration is 15 seconds. Within that period, a total of approximately 500,000 bytes of raw data will be accumulated from all 16 channels. Since this is much larger than the read-write memory capacity of the minicomputer, these data are stored on the RK05 high-speed hard disk as it is accumulated during the atomization. The disk controller hardware allows disk transfers to be accomplished without processor intervention once initiated.

The processing of the raw intensity data from each atomization is performed in the time interval between atomizations when the atomizer is cooling down and then drying and ashing the next sample. These steps normally take 1–2 minutes.

The data processing requirements can be broken down into three steps:

1. Computation of a separate absorbance-time array for each channel.

2. Measurement of peak area and/or peak height.

3. Construction and use of analytical curves in the computation of analytical concentrations.

The unexpectedly superior signal-to-noise properties of SIMAAC can be demonstrated by implementation of only step 1 noted above. The program is written in Fortran with assembly language subroutines to access the raw data on disk. The most sensitive (best signal to noise ratio (S/N)) method of calculating absorbance is as follows. The data are processed one channel at a time according to the scheme shown in FIG. 3(c). During each half-cycle of the modulation waveform, ten intensity readings are taken, five on the line and five off. Five intensity readings taken off the line are summed and called $I_o$. Five readings taken on the line are summed and called I. The program is written to account for the time delay (phase lag) between the applied torque motor driver waveform and the actual wavelength modulation waveform. It should be noted that the five readings which constitute one measurement of $I_o$ are split up into two groups of 2½ values each before and after a group of I values. This is necessary in order to reduce the effect of rapid changes in $I_o$ with time which occur due to the transient background absorption and light scattering from samples with complex matrices. Absorbance is then calculated as the common log of the ratio of $I_o$ to I. In this way, one value of absorbance is calculated for every half-cycle of the modulation waveform, i.e., for every ten intensity headings. Approximately 112 absorbances are computed per second per channel. These absorbance values are stored as a one-dimensional array for further processing. The absorbance arrays for the other channels are obtained in the same way.

Absorbance may also be calculated in ways which are less sensitive, but which provide calibration curves which are linear at higher analyte concentrations. These "reduced sensitivity" absorbance values can be determined from the same set of raw data which is used to calculate the most sensitive absorbance values described in the preceeding paragraph. The "reduced sensitivity" absorbance values are determined as follows: Ten intensity readings are taken for each half cycle of the torque motor which corresponds to a single sweep over the absorption profile. This is done in such a manner that points 1 and 10 correspond to the two extremes, off the side of the profile at opposite ends, and points 5 and 6 are the two middle points, at the center of the absorption profile. Points 1 and 10 are summed and assigned the value of $I_o$. For I, it is possible to use the sums of points 5 and 6, or 4 and 7, or 3 and 8, or 2 and 9. The computed absorbance will be most sensitive (largest) for pair 5 and 6 and least sensitive (smallest) for 2 and 9. Each succeeding pair (5 and 6; 2 and 9) provides a linear calibration for higher analyte concentrations. Since symmetry is preserved, the "less sensitive" absorbance values are also background corrected and minimize the effect of flicker noise. Use of all methods of computing absorbance results in a family of curves, from the same set of raw data, which covers 5 to 6 orders of magnitude of concentration.

In the SIMAAC system it was found that the major noise source was photon shot noise at low concentrations. Lamp fluctuation noise and background absorption fluctuation noise were expected to be reduced or eliminated by the wavelength modulation and ratio calculation. Atomizer background emission noise and analyte emission noise were made negligable by the comparatively high brightness of the Eimac lamp and the comparatively small entrance slit area of the echelle polychromator. In the presence of high background (matrix) absorption, electronic noises became important.

The noise characteristics of SIMAAC were studied by measuring four different signals as a function of wavelength and/or source intensity. These four signals were: the electronic noise $\sigma_E$; the electronic noise with the furnace in the atomization cycle; and the $I_o$ noise, $\sigma I_o$ measured with and without wavelength modulation.

The electronic noise, $\sigma_E$, was measured with the Eimac lamp and the graphite furnace off. The major components were amplifier noise, ADC digitization noise, and photo-multiplier tube (PMT) dark current noise. The noise contributed by the amplifier and the PMT dark current varied between elements depending on the amplifier gain and the PMT voltage. The digitization noise was constant for all channels, 0.72 mV, as determined by the magnitude of the quantization level of the 12 bit ADC, 2.4 mV. The electronic noise was measured simultaneously for eight channels using the data acquisition scheme described previously (the PMT signal for each element is sampled at 1.12 kHz). $\sigma_E$ was calculated from the standard deviation of ten signal measurements, each the average of 3,840 ADC readings. For a combined analog-digital system the noise bandwidth, $\Delta f$, has been defined as $1/(4\tau n)$ where $\tau$ is the standard analog RC filter time constant and n is the number of analog to digital conversions averaged. It was assumed that at least $2\tau$ is allowed between conversions of the same signal to ensure that the two values are independent of each other. For SIMAAC, $\tau = 0.1$ ms for the PMT-ADC interface circuit and each signal is measured every millisecond. Consequently, for n=3,840, the noise bandwidth for each determination is 0.65 Hz.

Figure 4:
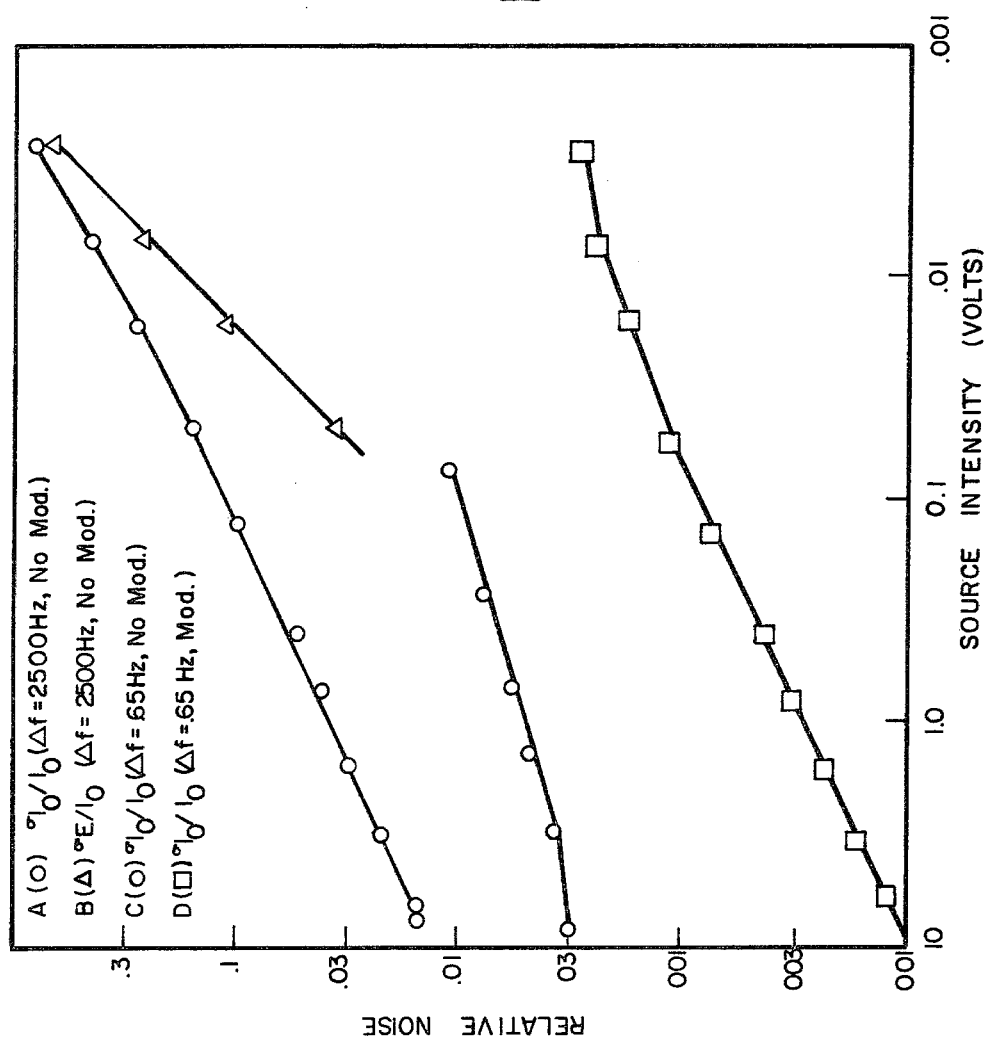
FIG. 4 is the noise expressed as relative standard deviation as a function of source intensity,
 A. (o) $\sigma I_o/I_o$ ($\Delta f=2500$ HZ, no modulation),
 B. ($\Delta$) $\sigma E/I_o$ ($\Delta f=2500$ Hz, no modulation),
 C. (o) $\sigma I_o/I_o$ ($\Delta f=-0.65$ Hz, no modulation),
 D. ($\square$) $\sigma I_o/I_o$ ($\Delta f=0.65$ Hz, modulation at 112 Hz); and, FIG. 5 is the family of absorbance curves for Ca (422.6 nm) in a flame, brackets showing the range of values for six determinations.

Since the electronic noise is constant for a given set of parameters, the relative electronic noise $\sigma_E/I_o$ will vary inversely with the source intensity. This is shown in FIG. 4, for example, for Cr (357.9 nm).

The electronic noise was also measured with the Eimac lamp off and the graphite furnace on, in order to determine the effect of furnace emission noise. With the furnace on, the noise levels ranged from comparable to 50% larger than the previously measured electronic noise. The increased noise levels were observed for elements with high PMT voltages and amplifier gains. The emission signal, along with the PMT dark current (the interface circuit was zeroed with current-to-voltage collector open), act in a manner analogous to stray light. The effect on the absorbance signal is minimal until high source attenuation (background absorbance of 2.0 or higher) occurs.

The $I_o$ noise, $\sigma I_o$, was determined with the Eimac lamp on and the graphite furnace off. The $I_o$ noise is composed of electronic noise, photon shot noise, and lamp flicker noise. To emphasize the advantages of wavelength modulation in minimizing the flicker component, the $I_o$ noise was measured in two different modes.

The first approach was to measure $I_o$ noise in transmittance units as a function of $I_o$, without wavelength modulation. This was done at two noise bandwidths. Initially $\sigma I_o$ was determined from 768 analog-to-digital conversions ($\Delta f = \frac{1}{4}\tau n = 2500$ Hz, where $\tau = 0.1$ ms and n=1). As shown for Cr (357.0 nm) in FIG. 4, plot A, the log of $\sigma I_o/I_o$ has a slope of $-0.47$ as a function of the log of $I_o$. This slope closely approximates that of a shot noise limited system ($-0.5$), despite the presence of the Eimac flicker noise which has been documented by Cochran and Hieftje. The minimal influence of the flicker noise is a consequence of the large noise bandwidth. Next, $\sigma I_o$ was computed from 10 values, each of which was the average of 3,840 conversions ($\Delta f = 0.65$ Hz where $\tau = 0.1$ ms and n=3,840). At this lower bandwidth, lamp flicker noise is expected to become more important, because the $1/f$ component of the flicker noise is not much reduced by the reduced bandwidth, whereas the white shot noise decreases proportionally with the square root of bandwidth. For this case, $\Delta f = 0.65$, the log of $\sigma I_o/I_o$ gives a maximum slope of $-0.29$ (FIG. 4, plot D) as a function of the log of $I_o$. At high source intensities, the slope approaches zero, as would be expected if source flicker noise becomes dominant. Thus the source flicker noise is important at lower bandwidths.

The second approach was to calculate $\sigma I_o/I_o$ from the absorbance baseline noise with wavelength modulation ($\sigma I_o/I_o = \sigma_A/0.43$). Absorbance values are computed at a frequency of 112 Hz. Cochrane and Hieftje have shown that the 1/f component of the Eimac flicker noise is observed at frequencies below 40-50 Hz. Consequently, compensation for this 1/f component is expected. This was verified experimentally as shown for Cr (357.9 nm) in FIG. 4, plot B. $\sigma_A$ was determined from 10 values each of which was the result of 3,840 conversions (f=0.65 Hz). The slope of the log of $\sigma I_o/I_o$ as a function of the log of $I_o$ is $-0.5$. These results indicate that the lamp flicker noise is predominantly of low-frequency (1/f) character and that wavelength modulation successfully compensates for this component of noise.

All the elements measured showed noise responses similar to Cr (FIG. 4). Each element had a slope of $-0.5$ when the log of the baseline absorbance noise was plotted as a function of the log of the source intensity. The plots were offset vertically depending on whether the Eimac was more or less intense than at the Cr wavelength (357.9 nm). The SIMAAC is shot noise limited for all elements near the detection limit. As analyte absorbance increases, analyte concentration fluctuation noise will become dominant. Near the detection limit, the shot noise limited case persists until the source attenuation, which would occur for high salt samples, reaches the point where electronic noise becomes significant. For Cr (357.9 nm) this transition occurs after the source has been attenuated by a factor of 250 whereas for Zn (213.9 nm), at which wavelength the Eimac is much less intense, the transition occurs after 70 fold attenuation of the source.

As will be shown hereinafter, SIMAAC sensitivities are comparable to conventional AAS sensitivities. Consequently, a comparison of SIMAAC noise levels to those of other systems is informative. Table I compares the electronic and Io noise of SIMAAC, another multielement AAS, and a Varian Techtron AA-6. For SIMAAC, $\sigma I_o/I_o$ computed from baseline absorbance noise, the comparison shows the expected wavelength dependence. The Eimac lamp has a maximum intensity at 500 nm and is almost three orders of magnitude less intense at 198 nm. SIMAAC shows comparable noise levels around 280 nm, lower noise levels at higher wavelengths, and higher noise levels at lower wavelengths. This trend is identical to that observed in earlier studies where the photon flux at the photodetector was compared for the Eimac-echelle system and a typical line-source system consisting of a hollow cathode lamp (HCL) and a ½ meter Ebert monochromator. As a result, one expects SIMAAC to have detection limits equal to or better than those of line-source AAS for elements above 280 nm and poorer detection limits below 280 nm. However, due to the square-root relationship between photon shot noise and intensity, the degradation in detection limits at shorter wavelengths is modest and in most cases is less than the uncertainty in measuring the detection limits.

A comparison of the signal-to-noise ratios between the single element, analog CEWM-AA and the multielement, digital SIMAAC will reveal any loss in capabilities associated with the conversion from the single element to the multielement analytical mode. A degradation of the analytical capabilities can arise from three possible sources: (1) The difference in optical paths (the multielement versus the single element exit slit cassettes), (2) The difference in the data acquisition systems (high frequency multiplexed digital sampling versus continuous analog measurement), and (3) The use of compromise analytical conditions for multielement analyses.

The variation in the optical paths between single element and multielement operation lies in the use of the multielement exit cassette and the wavelength modulation. Significant differences in signal intensity absorbance can arise for several reasons. First, the multielement cassette uses pin-head mirrors for all but five elements of the twenty in the present cassette (Se 196.0 nm, Sn 224.6 nm, Ca 239.8 nm, V 318.5 nm, and Na 330.2 nm) to reflect the light from the exit slits to the appropriate PMT. Spectrametrics has reported a 25% loss in intensity as a result of these mirrors. With a shot noise limited system, this corresponds to a 13.4% decrease in the signal-to-noise ratio. This degradation has not been experimentally verified.

Ideally, the focal plane of the echelle is flat and superimposed on the plane of the exit cassette. If not, then poorer resolution and decreased analytical sensitivity (increased characteristic concentration) will be observed for at least some of the channels. The data in Table II allow the resolution of the single element and multielement modes to be compared. In each case, the full width at half height (FWHH) was determined for hollow cathode lamp emission lines using a mechanical scanning device. In general, the resolution in the multielement mode is comparable to that of the single element mode, however, a trend is visible. Resolution in the multielement mode becomes comparatively worse at higher wavelengths.

Finally, in order to have maximum sensitivity for all elements simultaneously, the exit slits on the multielement cassette must be aligned such that they all rest on their respective absorption peaks at the same time. The overall alignment of the spectrum at the focal plane with respect to the exit slit cassette can be controlled by the operator from the front panel wavelength controls and can be fine tuned at any time if necessary. The internal alignment of one exit slit with respect to the others is set when the cassette is manufactured and cannot be modified by the user. This alignment is performed adequately by the manufacturer of the echelle spectrometer. Wavelength drift has not been observed to be a significant factor.

The data acquisition systems of the two modes are drastically different. In the single element mode, absorbance is computed continuously by an analog circuit. This operational amplifier circuit simultaneously determines $I_o$ and I which are input to a log ratio module, providing a continuous absorbance output. In the multielement mode, the absorbance is computed digitally, as described hereinbefore, at the rate of 112 computations per second. The signal-to-noise ratios of the two methods were compared for the graphite furnace measurement of a 50 ppb Pb standard. Due to the rapid rate of absorbance calculation in the digital system, the effective electrical bandwidth of the digital system is much greater than that of the analog system. Consequently, a larger signal and a larger noise component are observed. The digital data acquisition system resulted in a 14% loss in the signal-to-noise ratio when sine wave modulation was used.

The use of the computer to drive the torque motor controller provides more freedom in selecting the modulation waveform. With analog circuitry, it is difficult to obtain any response from the torque motor other than a sine wave when frequencies greater than 50 Hz are used. The sinusoidal response of the torque motor results in the PMT signal being a distorted sine wave. The computer generated three step square wave, FIG. 2(a), produces a PMT signal which is closer to a square wave. Consequently, the result is an increase in the signal, the added versatility in generating the modulation waveform resulting in a net improvement of 30% in the signal-to-noise ratio for the multielement system.

In the single element mode, it is possible to optimize all instrumental parameters for the element being analyzed. For multielement analyses, though, it becomes necessary to select parameters which are either average values for the elements being analyzed or extreme values in order to protect the analytical integrity of one or more of the elements. These non-optimal, or compromise, analytical conditions result in reduced signal-to-noise ratios for some elements.

Surprisingly, relatively few compromises are necessary, for the SIMAAC system. The Eimac lamp is run at a near maximum current of 20 A. Unlike conventional AA systems where sensitivity is reduced at high hollow cathode lamp currents due to self absorption of the emission line, SIMAAC detection limits improve proportionally with the square root to the source intensity. Consequently, a maximum operating current for the Eimac is optimal for all elements.

Furnace atomization conditions are dictated by the elements being analyzed. The atomization temperature must be high enough that even the least volatile element is volatilized. The ashing temperature must be low enough that the most volatile element is not volatilized prematurely. Drying conditions are assigned to provide gentle evaporation of the solvent without scattering the sample about the interior of the furnace.

Three parameters on the echelle monochromator are variable: the entrance slit height and width (all exit slits were specified to be 25 $\mu$m wide and 300 $\mu$m high when the multielement cassette was ordered), and the modulation interval. The best resolution available is necessary to obtain maximum sensitivity for SIMAAC or CEWM-AAS. Consequently, 25 $\mu$m wide entrance and exit slits are routinely used. Slit heights of 300 $\mu$m are used as a compromise between intensity and order-overlap stray light. Optimum refractor plate modulation angles range from $\pm 3°$ to $\pm 5°$ using a sine wave. The corresponding wavelength modulation interval in nanometers varies with the dispersion of the monochromator. With stepped square wave modulation, the amplitude is considerably less critical. Consequently, little change in sensitivity is expected with a modulation angle as high as $\pm 20°$. This large amplitude of modulation permits measurements far off the line in order to significantly extend the linear operating range of SIMAAC.

The combined effect of all three factors, the optical path, the data acquisition system, and the compromise analytical conditions, is determined by comparing simultaneous multielement detection limits with those obtained in the single element mode. The simultaneous multielement detection limits were obtained using the following parameters: a 20 A Eimac lamp current; Furnace conditions of: a 20 S dry cycle with the temperature ramped from ambient to 150° C., to 10 A ash at 300° C., an 8 S atomization at 2800° C., (all temperatures as read from the HGA-2100 power supply); entrance slits of 25 $\mu$m $\times$ 300 $\mu$m, Ar sweep gas in the interrupt mode, and a modulation angle of $\pm 6°$. The results shown in Table III indicate that the detection limits for SIMAAC and CEWM-AAS do not differ significantly compared with the variation associated with individual run conditions.

The absolute detection limits and characteristic concentrations are listed in Tables III and IV, respectively. The absolute detection limit is defined as the amount of analyte, based on a 20 $\mu$l sample, for which the signal is twice the root mean square RMS noise of the baseline. The noise levels were measured just off the analytical line. The peak height method was used to calculate detection limits to conform with previous determinations. The absolute characteristic concentration is the amount of sample necessary to give an absorbance of 0.0044.

SIMAAC characteristic concentrations are comparable to those listed by Perkin-Elmer for the HGA-2100 with the exception of Fe which is approximately a factor of four worse. The Fe line at 302.0 nm is used for SIMAAC because although both lines (302.0 and 248.3 nm) give the same characteristic concentration, the lower noise levels at 302.0 nm (because of higher Eimac intensity) results in better detection limits.

A comparison of detection limits for SIMAAC, CEWM-AAS, commercially available line-sources AAS using electrothermal atomization, and induction-coupled plasma atomic emission spectrometry (ICP-AES) is shown in Table III. The range of values listed for SIMAAC and CEWM-AAS reflects the day-to-day variability of this parameter.

The range of values listed for commercially available AA systems reflects the range of detection limits reported in the art. None of these detection limits were obtained using background correction, which can result in a factor of 2 to 4 deterioration in the S/N ratio. The comparison to ICP-AES detection limits is complicated by the fact that the latter are normally reported in concentration units, while furnace detection limits are usually reported in absolute mass units. Thus the solution volume requirements for ICP-AES must be considered. The detection limits listed in Table III assume that the ICP requires 750 $\mu$l and 200 $\mu$l respectively for ultrasonic and pneumatic nebulization.

SIMAAC detection limits compare well with those listed for CEWM-AAS and commercially available AAS. Both SIMAAC and CEWM-AAS have detection limits for Zn which are an order of magnitude worse than those listed by Perkin-Elmer for the HGA-2100 (0.1 pg). This is at least partly due to the low intensity of the Eimac lamp in the UV region. However, the SIMAAC and CEWM-AAS detection limits for Zn agrees well with that determined by Sturgeon et al, using the same furnace with a commercially available line source AAS. For the elements reported here, SIMAAC detection limits are comparable to an order of magnitude better than ICP-AES absolute detection limits using ultrasonic nebulization and desolvation. Using pneumatic nebulization, ICP-AES is one to three orders of magnitude worse. (The concentration detection limits of SIMAAC, assuming a 20 $\mu$l sample size, are roughly comparable to those reported for ICP-AES with pneumatic nebulization using a much larger sample size.)

Figure 5:
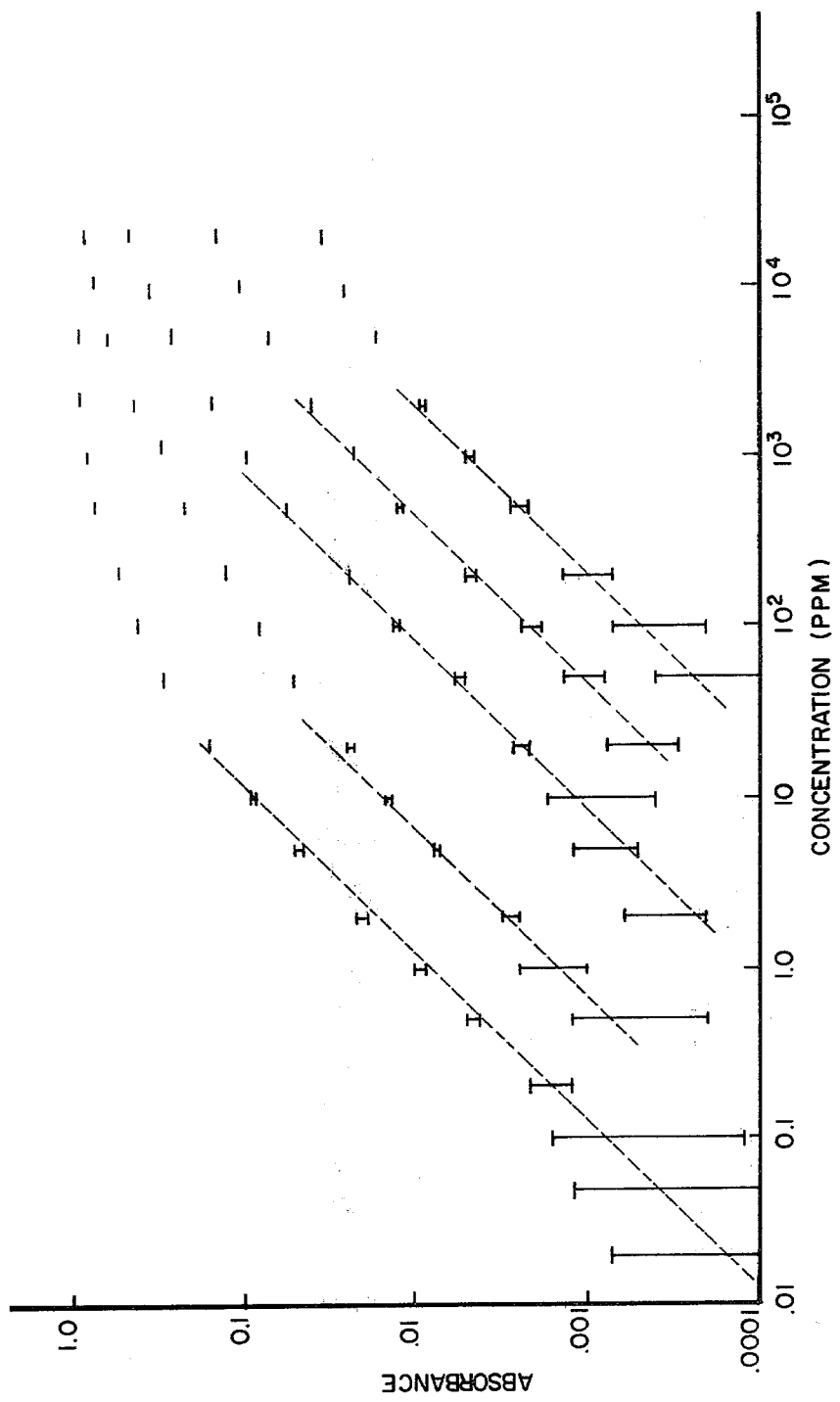

FIG. 5 shows an example of the family of calibration curves obtained from the same set of raw data. This data show the determination of Ca, 422.6 nm, with a flame atomizer. The wavelength modulation frequency was 56 Hz (still above the 50 Hz recommended as necessary to avoid lamp flicker noise). The computer sampling frequency was the same resulting in 20 sample points per element per half cycle of the torque motor. The three step square wave was modified slightly to allow the torque motor to be modulated at higher amplitudes. The Ca calibration curves cover approximately 6 orders of magnitude of concentration. The brackets show the range of values for six determinations.

The time resolution of SIMAAC is comparable to or better than most conventional AAS instruments. Under normal operating conditions, the SIMAAC samples each channel at a frequency of 1.12 kHz. As a result, 112 background corrected absorbance values are computed each second for each channel. Currently available analog, oscilloscope display systems offer only two fold better resolution for a single channel without background correction. From a qualitative point of view, the resolution of multielement CEWM-AAS appears to be sufficiently fast to allow characterization of the peak shape. The atomization of Zn at 2800 degrees is close to a worst case test of the system response. The width of the 5 ppb Zn peak was approximately 0.4 seconds, yet over 40 absorbance points were computed in its duration.

All of the tests conducted in connection with SIMAAC have demonstrated that the utilization of both a continuum source and wavelength modulation in multi-element atomic absorption analysis yield results which are comparable to single element analysis, rather than results which are even poorer than those obtained with either a continuum source or wavelength modulation, but not both, such poor results being such as would be expected by those skilled in the art.

The present invention may be embodied in other specific forms without departing from the spirit or essential attributes thereof, and accordingly, reference should be made to the appended claims, rather than to the foregoing specification as indicating the scope of the invention.

TABLE II-continued

COMPARISON OF SINGLE ELEMENT AND MULTIELEMENT MODE RESOLUTON

| | | FWHH (nm)[a] | | |
|---|---|---|---|---|
| Element | Wavelengths (nm) | Single Element | Multi-element | Resolution (nm)[b] |
| Fe | 302.1 | .0042 | .0046 | .0029 |
| Na | 330.2 | .0046 | .0053 | .0032 |
| Cr | 357.9 | — | .0058 | .0036 |
| Ca | 422.6 | .0056 | .0070 | .0043 |
| Na | 589.6 | .0085 | .0151 | .0066 |

[a]Experimental data using mechanical scanning, 25 um wide entrance and exit slits.
[b]25 um entrance and exit slits.

TABLE III

Absolute Detection Limits (pg)
(Standard resonance wavelengths except where noted.)

| Element | SIMAAC[a] (Multi-element) | CEWM-AAS[a] (Single Element) | CONVENTIONAL-AAS[b] (Single Element) | ICP-AES[c] (Multi-element) |
|---|---|---|---|---|
| Ba | — | 3[d] | 15 | 7.5–20[f] |
| Cd | — | 1–4 | .1–.5 | 63–500 |
| Co | 14–16 | — | 4–10 | 90–400[f] |
| Cr | 1.5–2.0 | .6–2 | 1–5 | 72–200[f] |
| Cu | 2.5–6.0 | 6–12 | 1–20 | 36–200 |
| Fe | 23–50[e] | 50[e] | 2–3 | 68–400[f] |
| Mg | .8 | .8 | .4 | 2.2–2C0[f] |
| Mn | 1–4 | 2–4 | 1 | 9–40[f] |
| Pb | — | 20–28 | 5–6 | 900–4,000[f] |
| V | 49–58 | — | 8–360 | 45–200[f] |
| Zn | 2–6 | 2–3 | .1–2.7 | 45–200 |

[a]This work; 20 μl sample size; range of values reflects uncertainty of detection limit determination and long-term variation in sensitivity due to normal variations in experimental conditions.
[b]5–100 μl sample sizes; range reflects extremes of listed values.
[c]The first figure shown in the best published detection limit using ultrasonic nebulization-desolvation and the second figure is that for pneumatic nebulization using 750 μl and 200 μl sample sizes, respectively.
[d]20 μl sample size.
[e]302.0 nm wavelength.
[f]Analytical wavelengths are non-resonance lines chosen for greater sensitivity.

TABLE I

Comparison of System Noise Sources

| | | Percent $I_o$ Noise | | | Percent Electronic Noise[5] | | Through put Ratios: Eimac-Echelle vs. |
|---|---|---|---|---|---|---|---|
| Element | Wavelength(nm) | SIMAAC[2] | TMMS[3] | V[4] | SIMAAC | TMMS[3] | HCL-0.5m Ebert Monochromator |
| Zn | 213.9 | .21 | .12 | .09 | .012 | .014 | .09 |
| Sn | 224.6 | .24 | — | — | — | — | — |
| Cd | 228.8 | — | .04 | .05 | — | .015 | .25 |
| Ni | 232.0 | .16 | .05 | .15 | .005 | .03 | .11 |
| Mn | 279.5 | .04 | .05 | .04 | .004 | .03 | .23 |
| Pb | 283.3 | — | .05 | — | — | .01 | .16 |
| Mg | 285.2 | .05 | .05 | .04 | .007 | .006 | 1.7 |
| Fe | 302.1 | .05 | — | — | .006 | 00 | 2.5 |
| Cu | 324.7 | .04 | .07 | .05 | .002 | .007 | 1.4 |
| Cr | 357.9 | .02 | — | — | .002 | — | 2.2 |
| Ca | 422.6 | .02 | — | — | .003 | — | 4.9 |
| Na | 589.6 | .02 | — | — | .004 | — | — |

[1]$\sigma_{Io}/I_o$ (or $\sigma'_{ri}/E'_r$ by convention of Bower and Ingle) × 100%
[2]$\sigma_{Io}/I_o = \sigma_A/0.43$.
[3]Time Multiplex Multiple Slit Multielement Flame AAS.
[4]Varian Techtron, AA-5.
[5]$\sigma_E/I_o$ (or $\sigma'_{ot}/E'_r$ by convention of Bower and Ingle) × 100%.

TABLE II

COMPARISON OF SINGLE ELEMENT AND MULTIELEMENT MODE RESOLUTON

| | | FWHH (nm)[a] | | |
|---|---|---|---|---|
| Element | Wavelengths (nm) | Single Element | Multi-element | Resolution (nm)[b] |
| Zn | 213.8 | .0024 | .0023 | .0019 |
| Ca | 239.4 | .0033 | .0023 | .0022 |
| Mn | 279.5 | .0039 | .0038 | .0026 |
| Mg | 295.2 | .0041 | .0027 | .0027 |

TABLE IV

Absolute Characteristic Concentrations (pg)[a]

| Element | SIMAAC | Perkin-Elmer |
|---|---|---|
| Co (240.7) | 13–15 | 44 |
| Cr (357.9) | 10–13 | 10 |
| Cu (324.7) | 9–21 | 22 |
| Fe (302.0) | 120–260 | — |
| (248.3) | — | 30 |
| Mg (285.2) | 3 | 3 |

TABLE IV-continued

| Absolute Characteristic Concentrations (pg)[a] | | |
|---|---|---|
| Element | SIMAAC | Perkin-Elmer |
| Mn (279.5) | 2–8 | 5 |
| V (318.5) | 350–410 | 400 |
| Zn (213.9) | 1–3 | 1 |

[a] Analyte in pg necessary to give .0044 absorbance.

We claim:

1. A method for simultaneous, multi-element, atomic absorption analysis of a plurality of known elements, comprising the steps of:

atomizing a sample for which quantities of the plurality of known elements are to be simultaneously determined;

illuminating the atomized sample with a continuum light source;

directing the resultant light through a high resolution polychromator, having an entrance aperture, while wave length modulating the light at a point behind the entrance aperture;

detecting light simultaneously, at a sampling frequency greater than ten times the modulation frequency times the number of elements to be analyzed, at a plurality of locations on the focal plane of the polychromator, each of the locations corresponding to a wavelength uniquely identifying an absorption peak for one of the elements, and converting the light into amplified electrical signals corresponding to the intensities of the light, the period of electrical signal acquisition being much smaller than the period of wavelength modulation and the period of wavelength modulation being much smaller than the duration of the shortest transient absorption signal;

coordinating the wavelength modulation and the light detection so that multiple acquisitions of data are made for each of the elements during each modulation cycle, the multiple acquisitions being made in a pattern symmetrically distributed on and about the centers of each of the wavelengths defining the absorption peaks, a ratio of the acquisitions on and off each of the absorption peak wavelengths providing a measure of absorbance for each of the elements; and, storing at least one of:

instantaneous levels of the electrical signals from which the ratios can be determined; and, the ratios, which can be determined during the sampling and detection, whereby the analytical results demonstrate improved quality, improved stability, correction for even and sloped background interferences and a useful analytical range extended by at least five orders of magnitude.

2. The method of claim 1, wherein the wavelength modulation is accomplished by rotating a quartz refractor plate.

3. The method of claim 1, wherein the light is detected through an array of exit apertures and an array of photomultiplier tubes.

4. The method of claim 1, wherein a computer is utilized to acquire and store said data.

5. The method of claim 1, wherein all of the multiple data acquisitions are used in formulating the ratios.

6. The method of claim 1, wherein only symmetric pairs of oppositely disposed data acquisitions are used in formulating the ratios.

7. The method of claim 1, further comprising the step of inspecting the absorption peak of each of the elements by displaying the ratios as a function of wavelength.

8. The method of claim 2, wherein the quartz refractor plate is rotated in response to a three-step wave form.

* * * * *